(12) United States Patent
Chinchoy et al.

(10) Patent No.: US 10,856,754 B2
(45) Date of Patent: Dec. 8, 2020

(54) INTRAUTERINE BALLOON APPARATUS, SYSTEM, AND METHOD FOR AUGMENTING UTERINE BIRTHING FORCES DURING PARTURITION

(71) Applicant: 3VO Medical, Inc., Studio City, CA (US)

(72) Inventors: Ed Chinchoy, Studio City, CA (US); Jay Snell, Los Angeles, CA (US); James Kelley, Coon Rapids, MN (US)

(73) Assignee: 3VO MEDICAL, INC., Studio City, CA (US)

( * ) Notice: Subject to any disclaimer, the term of this patent is extended or adjusted under 35 U.S.C. 154(b) by 135 days.

(21) Appl. No.: 16/238,431

(22) Filed: Jan. 2, 2019

(65) Prior Publication Data

US 2019/0133475 A1 May 9, 2019

Related U.S. Application Data

(63) Continuation of application No. 14/942,748, filed on Nov. 16, 2015, now Pat. No. 10,206,595.

(Continued)

(51) Int. Cl.
*A61B 17/42* (2006.01)
*A61B 5/04* (2006.01)
(Continued)

(52) U.S. Cl.
CPC ............... *A61B 5/04* (2013.01); *A61B 5/035* (2013.01); *A61B 5/065* (2013.01); *A61B 5/4356* (2013.01);
(Continued)

(58) Field of Classification Search
CPC ........... A61B 5/033; A61B 5/035; A61B 5/04; A61B 5/04882; A61B 5/065;
(Continued)

(56) References Cited

U.S. PATENT DOCUMENTS

| 3,230,953 A | 1/1966 | Birnberg et al. |
| 3,918,444 A | 11/1975 | Hoff et al. |

(Continued)

OTHER PUBLICATIONS

European Patent Appln. No. 16866883.8. Extended European Search Report (dated Apr. 8, 2019).

(Continued)

*Primary Examiner* — Melanie R Tyson
(74) *Attorney, Agent, or Firm* — Loza & Loza, LLP; David S. Sarisky

(57) ABSTRACT

An intrauterine balloon apparatus to augment uterine birthing forces and assist fetal descent during parturition is provided. The body of the balloon apparatus begins packaged in a compressed state minimizing volume, enabling delivery through the birth canal. The apparatus is advanced to a proximal uterine location and deployed for operation by introducing a pressurized agent through its conduit, causing the body to expand and apply directional forces towards the infant and birth canal. The balloon body is shaped to apply pressures dispersed towards the infant and the bidirectional conduit enables fluid conduction as the infant descends. After the infant has successfully descended and been delivered through the birth canal, pressure within the balloon body is relieved through the conduit thereby collapsing the volume of the balloon body and enabling retraction through the birth canal.

10 Claims, 7 Drawing Sheets

Related U.S. Application Data

(60) Provisional application No. 62/080,511, filed on Nov. 17, 2014, provisional application No. 62/080,506, filed on Nov. 17, 2014.

(51) Int. Cl.
*A61B 5/00* (2006.01)
*A61B 5/03* (2006.01)
*A61B 5/06* (2006.01)
*A61B 17/00* (2006.01)

(52) U.S. Cl.
CPC .......... *A61B 5/4836* (2013.01); *A61B 5/6852* (2013.01); *A61B 5/6853* (2013.01); *A61B 17/4241* (2013.01); *A61B 2017/00292* (2013.01); *A61B 2017/00557* (2013.01)

(58) Field of Classification Search
CPC ..... A61B 5/4343; A61B 5/435; A61B 5/4356; A61B 5/4836; A61B 5/6852; A61B 5/6853; A61B 17/42; A61B 17/4241; A61B 17/44; A61B 2017/00292; A61B 2017/00557; A61B 2017/445; A61B 2017/447
See application file for complete search history.

(56) References Cited

U.S. PATENT DOCUMENTS

| | | |
|---|---|---|
| 3,948,270 A | 4/1976 | Hasson |
| 4,089,337 A | 5/1978 | Kronner |
| 4,136,681 A | 1/1979 | Hon |
| 4,252,131 A | 2/1981 | Hon et al. |
| 4,338,943 A | 7/1982 | Okamoto et al. |
| 4,349,033 A | 9/1982 | Eden |
| 4,490,421 A | 12/1984 | Levy |
| 4,533,345 A | 8/1985 | Louw |
| 4,722,730 A | 2/1988 | Levy et al. |
| 4,775,362 A | 10/1988 | Kronner |
| 4,873,986 A | 10/1989 | Wallace |
| 4,890,623 A | 1/1990 | Cook et al. |
| 4,901,735 A | 2/1990 | Von Berg |
| 4,906,244 A | 3/1990 | Pinchuk et al. |
| 4,944,307 A | 7/1990 | Hon et al. |
| 4,976,692 A | 12/1990 | Atad |
| 4,996,974 A | 3/1991 | Ciarlei |
| 5,156,590 A | 10/1992 | Vilmar |
| 5,156,612 A | 10/1992 | Pinchuk et al. |
| 5,247,932 A | 9/1993 | Chung et al. |
| 5,279,308 A | 1/1994 | Disabito et al. |
| 5,304,131 A | 4/1994 | Paskar |
| 5,304,197 A | 4/1994 | Pinchuk et al. |
| 5,318,526 A | 6/1994 | Cohen |
| 5,373,852 A | 12/1994 | Harrison et al. |
| 5,377,673 A | 1/1995 | Van et al. |
| 5,449,371 A | 9/1995 | Pinchuk et al. |
| 5,507,725 A | 4/1996 | Savage et al. |
| 5,522,400 A | 6/1996 | Williams |
| 5,566,680 A | 10/1996 | Urion et al. |
| 5,573,007 A | 11/1996 | Bobo, Sr. |
| 5,624,399 A | 4/1997 | Ackerman |
| 5,738,653 A | 4/1998 | Pinchuk et al. |
| 5,741,320 A | 4/1998 | Thornton et al. |
| 5,785,053 A | 7/1998 | Macandrew et al. |
| 5,865,800 A | 2/1999 | Mirarchi et al. |
| 5,865,801 A | 2/1999 | Houser |
| 5,947,991 A | 9/1999 | Cowan |
| 5,951,497 A | 9/1999 | Wallace et al. |
| 5,984,879 A | 11/1999 | Wallace et al. |
| 5,991,649 A | 11/1999 | Garfield et al. |
| 6,002,968 A | 12/1999 | Edwards |
| 6,036,697 A | 3/2000 | Dicaprio |
| 6,110,142 A | 8/2000 | Pinchuk et al. |
| 6,129,737 A | 10/2000 | Hamilton et al. |
| 6,146,355 A | 11/2000 | Biggs |
| 6,231,524 B1 | 5/2001 | Wallace et al. |
| 6,356,777 B1 | 3/2002 | Garfield et al. |
| 6,395,012 B1 | 5/2002 | Yoon et al. |
| 6,434,418 B1 | 8/2002 | Neal et al. |
| 6,520,977 B2 | 2/2003 | Piraka |
| 6,522,933 B2 | 2/2003 | Nguyen |
| 6,592,550 B1 | 7/2003 | Boatman et al. |
| 6,648,842 B2 | 11/2003 | Horkel |
| 6,676,680 B1 | 1/2004 | Packer |
| 6,694,192 B2 | 2/2004 | Policker et al. |
| 6,743,227 B2 | 6/2004 | Seraj et al. |
| 6,802,825 B2 | 10/2004 | Ackerman et al. |
| 6,827,703 B1 | 12/2004 | Ackerman |
| 6,843,251 B1 | 1/2005 | Huerland et al. |
| 6,879,858 B1 | 4/2005 | Adams |
| 6,979,312 B2 | 12/2005 | Shimada |
| 7,029,467 B2 | 4/2006 | Currier et al. |
| 7,220,252 B2 | 5/2007 | Shah |
| 7,309,324 B2 | 12/2007 | Hayes et al. |
| 7,333,844 B2 | 2/2008 | Jones et al. |
| 7,481,774 B2 | 1/2009 | Brockway et al. |
| 7,695,451 B2 | 4/2010 | Bencini et al. |
| 7,708,716 B2 | 5/2010 | Shah |
| 7,720,517 B2 | 5/2010 | Drysen |
| 8,123,773 B1 | 2/2012 | Shirley |
| 8,206,343 B2 | 6/2012 | Racz |
| 8,221,401 B2 | 7/2012 | Sharkey et al. |
| 8,292,901 B2 | 10/2012 | Auerbach et al. |
| 8,491,503 B2 | 7/2013 | Zaiken et al. |
| 8,597,306 B1 | 12/2013 | Blurton et al. |
| 8,606,371 B2 | 12/2013 | Garfield et al. |
| 8,690,873 B2 | 4/2014 | Truckai et al. |
| 8,900,215 B2 | 12/2014 | Pepper et al. |
| 8,945,025 B2 | 2/2015 | Olson et al. |
| 8,972,028 B2 | 3/2015 | Garfield et al. |
| 2005/0038421 A1 | 2/2005 | Joyce et al. |
| 2008/0215031 A1 | 9/2008 | Belfort et al. |
| 2008/0300571 A1 | 12/2008 | Lepivert |
| 2011/0028981 A1 | 2/2011 | Mckay |
| 2011/0082488 A1 | 4/2011 | Niazi |
| 2012/0078039 A1 | 3/2012 | Tai et al. |
| 2012/0109177 A1 | 5/2012 | Ulmer |
| 2013/0190796 A1 | 7/2013 | Tilson et al. |
| 2013/0253466 A1 | 9/2013 | Campbell et al. |
| 2013/0261702 A1 | 10/2013 | Garfield et al. |
| 2014/0277053 A1 | 9/2014 | Wang et al. |
| 2015/0164401 A1 | 6/2015 | Toth et al. |

OTHER PUBLICATIONS

PCT/US16/61429. International Search Report (dated Mar. 25, 2017).
PCT/US16/61429. Written Opinion (dated Mar. 24, 2017).
PCT/US2016/061354. International Preliminary Report on Patentability (dated Jan. 18, 2018).
PCT/US2016/061429. International Preliminary Report on Patentability (dated Jan. 18, 2018).

INTRAUTERINE BALLOON APPARATUS, SYSTEM, AND METHOD FOR AUGMENTING UTERINE BIRTHING FORCES DURING PARTURITION

CROSS-REFERENCE TO RELATED APPLICATIONS

This application is a continuation application of U.S. patent application Ser. No. 14/942,748, filed Nov. 16, 2015, entitled "Intrauterine Balloon Apparatus, System, and Method for Augmenting Uterine Birthing Forces During Parturition," now U.S. Pat. No. 10,206,595, which claims the benefit of U.S. Provisional Application Ser. No. 62/080,511, entitled "Intracorporeal Birthing Device" and filed on Nov. 17, 2014, and U.S. Provisional Application Ser. No. 62/080,506, entitled "Birthing Assistance Catheter" and filed on Nov. 17, 2014, each of which is expressly incorporated by reference herein in its entirety.

This application includes subject matter related to U.S. patent application Ser. No. 14/942,577, filed on Nov. 16, 2015, entitled "Intrauterine Access Catheter for Delivering and Facilitating Operation of a Medical Apparatus for Assisting Parturition," now U.S. Pat. No. 10,1005,070, which is expressly incorporated by reference herein in its entirety.

BACKGROUND

Field

The present disclosure relates generally to the field of obstetrics, and more specifically, to a medical balloon apparatus and system for assisting infant descent during parturition. The apparatus or system can be used during any stage for a full term pregnancy, and is particularly useful when insufficient uterine contractile effectiveness is diagnosed resulting in infant descent latency (i.e. dystocia, or the "failure to descend") and when coordinated mechanical assistance to aid infant descent is desired.

Background

There are three physiologic stages of labor during the intrapartum process of natural childbirth. The first stage is latent labor and begins when the uterine muscles begin to tighten (contract) and relax in a periodic manner. These early contractions occur at an irregular frequency each lasting for less than a minute and are known to be uncomfortable for the mother. The total duration of this first phase is highly variable and last from several hours to several days. Over time frequency of the contractions becomes more regular and grows with intensity, resulting in increased intrauterine pressures and associated pain, causing greater downward forces towards the infant and birth canal leading to the thinning (effacing) and opening (dilation) of the cervix.

The second stage is active labor and begins when the mother's uterine contractions become more regular and frequent, generating sufficient coordinated strength towards the infant and birth canal causing the cervix to become thinner and diameter to grow larger for the infant to begin descending down the birth canal. The combination of intensifying uterine contractions, increased intrauterine pressures, and reduced birth canal resistance promotes gradual infant descent through the birth canal until it is eventually delivered or surgically extracted. The duration of this stage lasts several hours and is associated with active infant movement and significant maternal pain. The third stage follows the delivery of the infant after which uterine contractions and the intrapartum process continues resulting in the expulsion of the placenta.

Difficulties often arise during the first and second stage when the mother's uterus is unable to generate the required contractility to initiate and ensure steady progression of the infant down the birth canal. Furthermore, increased resistance to infant descent by the mother's pelvic region along the birth or cervical canal requires greater effective birthing forces to ensure infant descent. A significant percentage of women therefore experience prolonged durations of labor which subsequently extends morbidity and increases the risks to both her and her infant due to extended physical stress.

A significant clinical need exists to manage intrauterine birthing forces for the purposes of assisting, stabilizing, or accelerating the birthing process during the first and second stage of labor. Currently, when a mother experiences prolonged durations of labor, the mainstay pharmacologic intervention used is synthetic Oxytocin (Pitocin) for stimulating and increasing uterine contractions. Dosages are based on protocols derived from a combination of population data and individual patient assessments of contraction rates and birthing progress, but individual patient's intrauterine pressures are generally not optimized on a per case basis. Although a very small minority of patients do receive intrauterine pressure monitors for titrating titrating Oxytocin, labor management using individual pressure optimization is not widely accepted due in large part to data suggesting pharmacologic interventions are limited with their effectiveness to achieve sufficient pressures. Other methods of assisting the birthing process include prostaglandins and Pessary cervical dilators to reduce the resistance of the birth canal to infant descent but do not compensate for ineffective uterine contractions.

In totality these interventions prove to be only marginally effective, and a significant percentage of mothers attempting natural births eventually undergo a surgical extraction of the infant (Cesarean) through a transverse abdominal incision to directly access the uterine cavity. Because Cesarean surgical interventions are highly invasive and result in extensive maternal morbidity, an increase of recovery times, and significantly greater risks of uterine injury with future subsequent births, a clinical need exists for providing an alternative option in lieu of a Cesarean section intervention by safely enhancing uterine descent forces and reducing labor durations.

SUMMARY

Disclosed herein is an intrauterine medical balloon apparatus, system, and method for obstetric applications to assist infant descent through the birth canal during parturition by augmenting uterine birthing forces. The apparatus applies forces towards the infant and birth canal to augment the effectiveness of natural physiologic uterine contractions. The apparatus is placed in a proximal uterine location to the infant and birth canal. A pressurized agent is introduced into the apparatus causing the apparatus to expand and apply directional pressure dispersed towards the infant. The medical balloon apparatus may be used during any stage of active labor, but particularly when one or more pathological periods of latency is diagnosed (dystocia, or the "failure to descend") or pathological uterine contractile effectiveness is diagnosed during the first or second stage of labor and sufficient cervical dilation has occurred.

In one aspect, a medical balloon apparatus includes a conduit body having a proximal region, a distal region, and an internal lumen. The medical balloon apparatus also includes a balloon body coupled to the distal region of the conduit. The balloon body has an internal chamber in fluid communication with the internal lumen of the conduit. The balloon body is configured to be placed in an intrauterine cavity at a location between an infant and uterine walls, and is further configured to operate, e.g., transition between a compacted state and an expanded state, there from. When in the expanded state the balloon body applies a force to a base of the infant in the direction of the cervical canal.

In another aspect, a medical balloon apparatus is configured to transition between a collapsed state and an expanded state. The medical balloon apparatus includes a conduit body having a proximal region, a distal region, and an internal lumen, and a balloon body coupled to the distal region of the conduit. The balloon body has an internal chamber in fluid communication with the internal lumen of the conduit, and includes a first wall and a second wall opposite the first wall. The balloon body is configured to expand to a shape wherein: the balloon body comprises an axis passing through the first wall and the second wall; during expansion of the balloon body, the first wall is displaced relative to the axis in a first direction, and the second wall is displaced relative to the axis in a second direction opposite the first direction; and the degree of displacement of the first wall is greater than the degree of displacement of the second wall.

In yet another aspect, a medical balloon apparatus is configured to fit at least partially within a lumen of an access catheter and to be deploy by sliding within the lumen. The medical balloon apparatus includes a balloon body having an internal chamber. The balloon body is configured to transition from a contracted state having a volume less than 10 ml and an external diameter less than 24 Fr (or 8 mm), to an expanded state upon introduction of a pressurized agent into the internal chamber. The balloon body has an exterior surface constructed with a low friction smooth biocompatible material with a coefficient of friction of less than 0.1 against the lumen of the access catheter.

In another aspect, a method of augmenting expulsive uterine forces towards a cervical canal during delivery of a fetus from a uterus, includes monitoring an intrinsic uterine contraction. The method further includes mediating a force generated via a medical balloon apparatus having a balloon body located in the uterus during the intrinsic uterine contraction. The force is directed toward the cervical canal and augments natural expulsive uterine forces, and mediating the force may include delivering pressurized agent to the balloon body to increase the force, or discharging agent from the balloon body to decrease the force.

In still another aspect, a system for augmenting expulsive uterine forces towards a cervical canal during delivery of a fetus from a uterus includes a medical balloon apparatus having a balloon body configured to be positioned in the uterus. The system also includes a controller coupled to the medical balloon apparatus and configured to monitor an intrinsic uterine contraction; and mediate a force generated via the balloon body during the intrinsic uterine contraction, wherein the force is directed toward the cervical canal and augments natural expulsive uterine forces. The controller may mediate the force by delivering pressurized agent to the balloon body to increase the force, or discharging agent from the balloon body to decrease the force.

DETAILED DESCRIPTION

Figure 1:
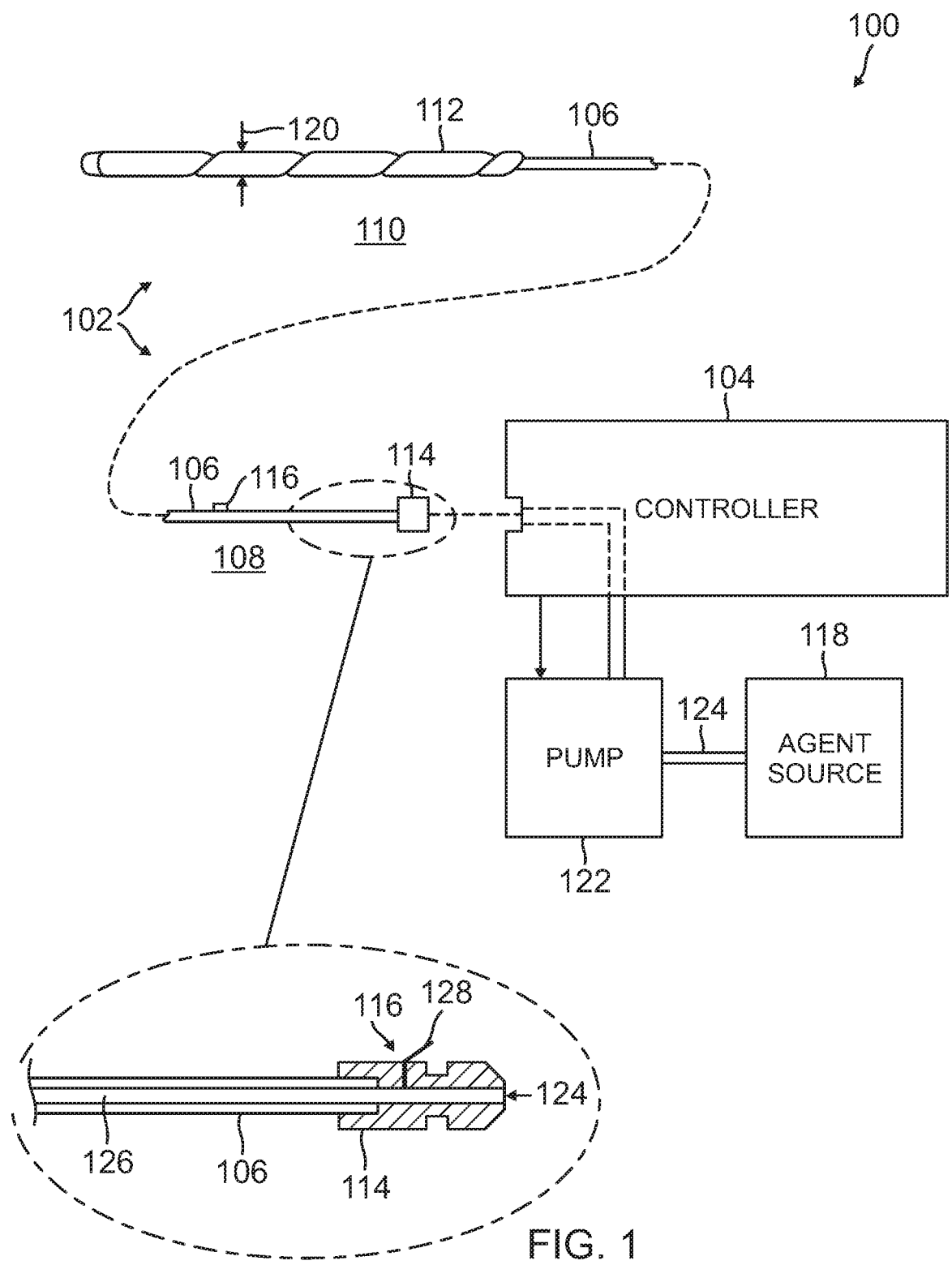
FIG. 1 is an illustration of a medical balloon system including a controller and a medical balloon apparatus in a collapsed, pre-deployed state.

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well known structures and components are shown in block diagram form in order to avoid obscuring such concepts.

Disclosed herein is an intrauterine medical balloon apparatus, system, and method to assist parturition. The objective of the apparatus, system, and method is to assist infant descent through the birth canal within the uterine cavity by augmenting intrinsic uterine birthing forces. The medical balloon apparatus includes a conduit body and a balloon body in fluid communication with each other. In use, the medical balloon apparatus is placed at an intrauterine location proximal to the infant and the birth canal, which may also be referred to as the cervical canal. Pressurized gas or fluid agent is conducted through the conduit body and into the balloon body causing the balloon body to expand. The balloon body is constructed so that a facet of the balloon body comes into contact with the infant during expansion of the balloon and applies pressure towards the base of the infant and towards the birth canal, thereby augmenting intrinsic uterine contraction forces and assisting infant descent through the birth canal.

In a configuration, the medical balloon apparatus is compatible for use with a catheter to access the uterine cavity via the cervix and navigate the infant, placenta, umbilical cord, and other intrauterine structures to the region of the fundus near the proximal end of the uterine cavity between the infant and endometrium lining. After reaching the target location, with the body of the balloon apparatus inline with the infant and birth canal at a proximal uterine location, a facet of the balloon body is placed adjacent the base of the infant. A pressurized gas or fluid agent is introduced into the proximal end of the conduit and conducted along the length of the conduit into the balloon body. The pressurized delivery of the agent can be timed in a synchronous manner to intrinsic uterine contractions resulting in expansion of the balloon body and application of forces towards the base of the infant and birth canal in-phase with natural maternal birthing forces. In one configuration, the conduit body conducts intra-balloon agent to a pressure sensor associated with the conduit body, e.g., at the distal end region of the conduit body. The conduit body may be attached to an external control unit and pressure signals obtained by the sensor may be provided to the control unit. The information on balloon pressure may be processed by the control unit to monitor intrauterine pressure and to time the delivery of the pressurized agent into the balloon body through the conduit so that the balloon body expands during intrinsic contractions and collapses in the absence of an intrinsic contraction. In an alternative configuration, the delivery of the pressurized agent is synchronized to an external measure of muscular activity caused by uterine contractions.

The proximal uterine cavity where the balloon body is placed, which may be defined by the space between the proximal uterine walls and the infant, expands as the infant descends. The balloon body is configured to expand correspondingly in both size and shape in order to proportionately fill the ongoing changes to the proximal uterine cavity shape, and augment the intrinsic pressure applied towards the infant and birth canal, while being further configured to limit the expansion of the balloon body against the surrounding uterine structures and uterine walls. The balloon body continues to expand until the infant is delivered or removed by a birthing professional.

Following successful vaginal delivery of the infant, the balloon body is deflated and the medical balloon apparatus is retracted through the birth canal and removed. The medical balloon apparatus can optionally be inflated and left in place to control excessive blood loss immediately following removal of the placenta.

FIG. 1 is an illustration of a medical balloon system 100 including a controller 104 and a medical balloon apparatus 102 in a collapsed, pre-deployed state. The medical balloon apparatus 102 includes a conduit body 106 having a proximal region 108 and a distal region 110. The medical balloon apparatus 102 also includes a balloon body 112 coupled to the distal region 110 of the conduit body 106, a coupling adapter or connector 114 at the proximal region 108 of the conduit body, and a relief valve 116. The relief valve 116 may be associated with the conduit body 106 in the proximal end region thereof, or may be integrated with the connector 114. The relief valve 116 may be configured to open automatically when pressure in the valve exceeds a threshold value. The relief valve 116 may also be configured to operate under control of an electrical signal, wherein the valve may be fully or partially opened and then closed in order to obtain or maintain a target internal pressure inside the medical balloon apparatus 102.

The conduit body 106 defines a hermetically sealed internal lumen 126 that traverses the length of the conduit body and is in sealed communication with the internal space of the balloon body 112. The conduit body 106 may be formed of high density polyethylene (HDPE), polytetrafluoroethylene (PTFE), polyethylene terephthalate (PET), polyester, polyether block amide (PEBA), polyurethane, polyimide, polyolefin, or nylon; and in one configuration has a length of at least 30 centimeters (cm). The connector 114 is configured to connect the medical balloon apparatus 102 to the controller 104 and provide an interface between the internal lumen 126 of the conduit body 106 and an agent source, such as a fluid/gas source 118, associated with the controller. The fluid/gas source 118 may be associated with the controller 104 through a pump 122, which may operate under control of the controller 104. The conduit body 106 enables bidirectional agent conduction between the agent source 118 and balloon body 112 through the internal lumen 126.

In operation, a pressurized agent, such as a gas or fluid agent 124 is delivered from the agent source 118, through the pump 122, into the controller 104, and then through the connector 114, into an internal lumen 126 defined by the conduit body 106. As previously described, the relief valve 116 may be located at the proximal end region of the conduit body 106, e.g., within the first 10 cm of the proximal region, or may be integrated with the connector 114. In either case, the relief valve 116 includes a deflectable member 128 that is configured by a pre-set resistance to deflect and thereby provide an opening through which gas or fluid agent 124 may be released from the internal lumen 126 into the ambient environment. Deflection of the deflectable member 128 may occur when the pressure within the internal lumen 126 exceeds a maximum pressure threshold. For example, the pressure threshold may be between 50-200 mmhg. In this sense, the relief valve 116 may function as an emergency relief valve that automatically releases agent from the balloon body 112 through the internal lumen 126 to thereby prevent over inflation of the balloon body.

As described further below with reference to FIG. 7 and FIG. 8, the medical balloon apparatus 102 operates within an intrauterine cavity to augment forces towards an infant during labor. To this end, the medical balloon apparatus 102 is configured to transition from the collapsed, pre-deployed state of FIG. 1, to an expanded or deployed state. While in a pre-deployed state, the medical balloon apparatus 102 may be delivered through the cervical canal so as to place the balloon body 112 in an intrauterine cavity, which may be defined by the space between an infant and uterine walls. To affect such delivery, the balloon body 112 may be contained within a compacted packaged format wherein the balloon body has an internal volume of less than 10 ml and an outer diameter 120 of less than 24 French (8 mm). In the expanded state, the balloon body 112 may assume a shaped that fits within the intrauterine cavity, and a size having a volume between 150 ml and 3000 ml and a maximum diameter between 5 cm and 20 cm. The balloon body 112 may be constructed from soft pliable biocompatible materials including one or more of silicone, polyurethane, polyvinyl chloride, latex, or mylar.

Transition of the balloon body 112 between a compacted state and an expanded state, and between different levels of expansion, may be controlled by the controller 104 based on one or more measures indicative of the state of intrinsic uterine contractions. The one or more measures may correspond to pressure measurements or electrical morphology measurements, and the intrinsic uterine contraction states represented by these measurements may include: a contraction onset, an increasing contraction stage during which contraction forces have increased, and a decreasing contraction stage during which contraction forces have decreased.

With respect to pressure measurements, the medical balloon apparatus 102 may include a pressure sensor that senses pressure within either the internal lumen 126 or the balloon body 112 and outputs an electrical signal corresponding to the measured pressure. Each of the pressure sensor and the relief valve 116 may be electrically coupled to an electrical contact of the connector 114. The controller 104 may be configured to receive a signal from the pressure sensor, process the received signal to obtain a corresponding pressure measurement, compare the pressure measurement to a threshold or target value, and output a control signal to the relief valve 116. In this case, as described above, the relief valve 116 may be configured to open and close under the control of the control signal from the controller 104.

Initially, the controller 104 may monitor pressure signals to detect for an onset of an intrinsic uterine contraction. To this end, upon delivery of the balloon body 112 to the intrauterine cavity, the controller 104 may deliver agent to the balloon body to partially expand the balloon body to facilitate pressure measurements by the pressure sensor associated with the conduit body 106. Thereafter, the controller 104 may compare measured pressures to a pressure value indicative of contraction onset. If a measured pressure exceeds the onset pressure value, the controller 104 may determine that a contraction onset has been detected and may deliver additional agent to the balloon body 112 to further expand the balloon body. An example onset pressure value may be a pressure greater than 0 mmhg, with typical pressure ranges of between 0-30 mmhg during initial stages of labor. During progressive labor, the pressures may increase up to 60-80 mmhg.

After detection of a contraction onset and initial expansion of the balloon body 112, the controller 104 may monitor the pressure signals and may mediate the delivery and discharge of fluid/gas to and from the balloon body based on such monitoring. For example, the controller 104 may control the relief valve 116 such that the relief valve discharges fluid/gas from the balloon body 112 when the sensed pressure exceeds the threshold value, such as 200 mmhg.

The controller 104 may also be configured to control the delivery of agent to the balloon body 112 and the discharge of agent from the balloon body such that expansion and contraction of the balloon body is synchronized to measured pressures. In this regard, the measured pressures are considered to relate to intrinsic uterine contractions, wherein an increase in a measured pressure indicates an increase in intrinsic contraction forces, while a decrease in measured pressure indicates a decrease in intrinsic contraction forces. Pressurized agent delivery is synchronized with intrinsic uterine contractions in order to augment with additive, versus subtractive, descent infant forces, and occurs in phase with other peripheral effects associated with effective uterine contractions during intrinsic contractions. These peripheral effects include secondary muscle recruitment and cervical dilatory responses to direct descent forces and reduce resistance to infant descent.

To affect synchronization of the expansion and contraction of the balloon body 112 to the measured pressure, the controller 104 may increase the delivery of agent in response to an increase in the measured pressure. The delivery of agent increases the expansion of the balloon body 112 and thereby augments the intrinsic uterine contraction forces. Conversely, the controller 104 may discharge agent in response to a decrease in the measured pressure. The discharge of agent results in contraction of the balloon body 112 and a corresponding reduction in the augmentative forces applied by the balloon. Controlling expansion and contraction of the balloon body 112 enables controlling the degree of excursions taken by the balloon wall towards the infant and birth canal per intrinsic uterine contraction, thereby limiting the rate of infant descent to clinically desired rates. The amount or degree by which forces provided by the balloon body 112 are either increased or decreased may be a function of the measured pressures.

To this end, the controller 104 may be programmed to monitor the measured pressures and to detect an intrinsic change in measured pressure that exceeds a threshold amount. An intrinsic change corresponds to a change that results from intrinsic uterine contraction activity. The change may be either an increase in pressure or a decrease in pressure. Upon detection of a change in pressure that satisfies the threshold criterion, the controller 104 may deliver or discharge a predetermined amount of agent in order to affect a further change in pressure.

For example, with respect to increasing pressure due to intrinsic uterine contraction activity, if the threshold pressure is P and the controller 104 detects an increase in intrinsic measured pressure that exceeds P, the controller may increase delivery of agent in order to cause the measured pressure to increase by a proportional amount of P, such as 10% of P, to obtain a current measured pressure $P_C$=P+0.10 P. The proportional increase in pressure causes the balloon body 112 to expand and augment the intrinsic uterine forces. The controller 104 may then monitor for further intrinsic increases in the measured pressure that satisfy a criterion and respond accordingly by delivering additional agent to further augment the increasing intrinsic uterine forces. The criterion may be a subsequent measured pressure that exceeds the current measured pressure $P_C$ by a threshold amount. The controller 104 may also incrementally and periodically increase the pressure within the balloon body 112 during a period of time that the measured pressure remains substantially constant, i.e., changes in measured pressures do not exceed the threshold. These incremental increases further augment the intrinsic uterine forces.

With respect to decreasing pressure due to intrinsic uterine contraction activity, the controller 104 may detect a decrease in intrinsic measured pressure that falls below a current measured pressure $P_C$ by a threshold amount. In this case, the controller 104 may discharge agent from the balloon body 112 in order to cause the measured pressure to decrease by a proportional amount of the current measured pressure $P_C$, such as 10% of $P_C$. The proportional decrease in pressure causes the balloon body 112 to contract in synchrony with the intrinsic uterine forces. The controller 104 may then monitor for further intrinsic decreases in measured pressure that satisfy a criterion and response accordingly by discharging additional agent from the balloon body 112.

One or more walls of the balloon body provide constructive augmentative forces towards the infant in phase with intrinsic uterine contractions, by pressurized delivery of agent through the conduit resulting in inflation and deflation of the balloon body in phase with intrinsic uterine contractile forces. The augmentative application of pressure thereby results in a similar intrauterine pressure morphology as the labor contractions caused by natural, unaided intrinsic physiologic uterine contractions.

With respect to electrical morphology signals that are indicative of the state of intrinsic uterine contractions, the controller 104 may receive electrical signals from an electrical sensor configured to monitor uterine muscular contractions. The electrical sensor may be part of the medical balloon apparatus 102 or may be an external sensor independent of the medical balloon apparatus that is directly connected to the controller 104. For example, electrical sensors may be located on a catheter that delivers the medical balloon apparatus. The controller 104 may be programmed to analyze the morphology of the electrical signals, to determine a contraction onset, an increasing contraction stage and a decreasing contraction stage. Based on these determinations, the controller 104 controls the initial delivery of agent to the balloon body and subsequent delivery and/or discharge of agent to/from the balloon body in the same manner as describe above with respect to the pressure senor configuration.

Figure 2:
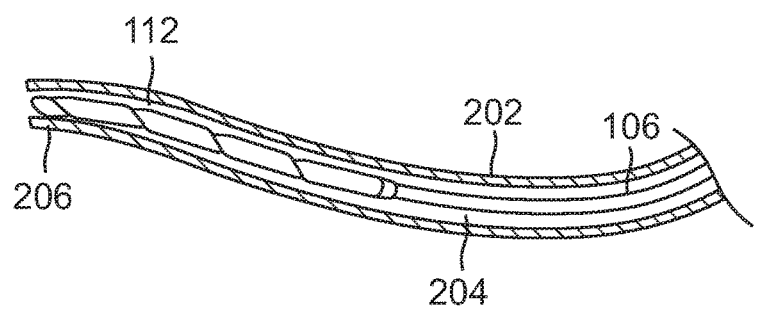
FIG. 2 is cross section illustration of a medical balloon apparatus positioned within a delivery catheter.

FIG. 2 is an illustration of a medical balloon apparatus 102 positioned within an access catheter 202. The balloon body 112 of the medical balloon apparatus 102 is packaged in a compacted format and shaped to fit within an elongated catheter lumen 204 of the access catheter 202. The access catheter 202 facilitates access and navigation to a targeted intrauterine cavity location. The access catheter 202 may be a catheter such as described in co-pending U.S. patent application Ser. No. 14/942,577, titled "Intrauterine Access Catheter for Delivering and Facilitating Operation of a Medical Apparatus for Assisting Parturition," the entire disclosure of which is herein incorporated by reference. The exterior surface of the balloon body 112 is configured to readily slide in a parallel direction within the catheter lumen 204 towards the distal end 206 of the access catheter 202 and outwards into the targeted location in the intrauterine cavity. To this end, the external surface of at least the distal region 110 of the medical balloon apparatus 102 may be coated with materials that increase lubricity of the external surface.

Figure 3:
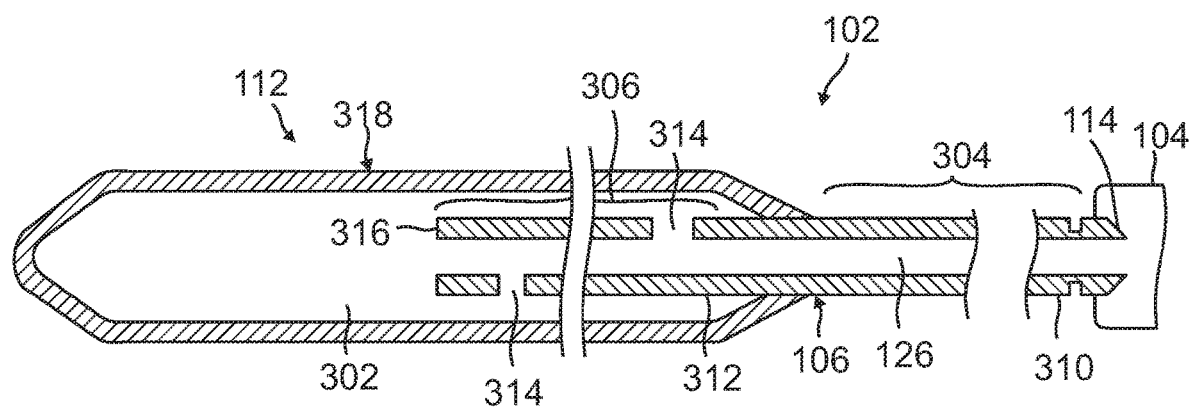
FIG. 3 is a cross section illustration of the medical balloon apparatus of FIG. 1.

FIG. 3 is a cross section illustration of the medical balloon apparatus 102 of FIG. 1. Although the balloon body 112 is in a collapsed state, it is illustrated in a spaced apart relationship relative to other elements for purposes of clarity. The balloon body 112 defines an internal balloon chamber 302. The conduit body 106 includes an external region 304, an internal region 306 within the internal balloon chamber 302, and an internal lumen 126 that traverses a length of the conduit body. The proximal end 310 of the conduit body 106 includes the connector 114 that is configured to connect to the controller 104. The distal end 316 of the conduit body 106 terminates approximately at the midpoint 318 of the balloon body 112.

The internal lumen 126 traverses the length of the conduit body 106, forming a hermetic sealed bidirectional fluid conduit between the balloon body 112 and the controller 104. The walls 312 of the internal region 306 of the conduit body 106 include one or more openings 314 that allow bidirectional fluid conduction from the agent source 118 through the controller 104 into the internal balloon chamber 302, and from the internal balloon chamber back into the conduit body 106. The internal lumen 126 communicates with the controller 104 through the connector 114 to provide a fluid communication path for delivery of a gas or fluid agent such as air or saline into the balloon body 112.

Figure 4:
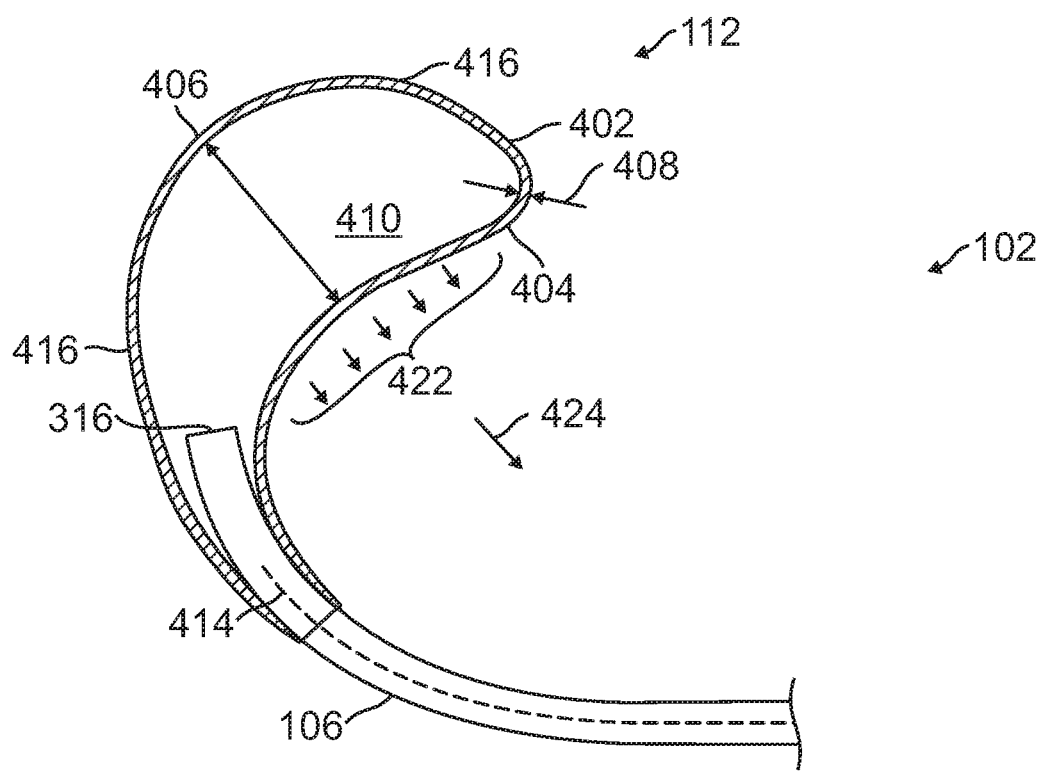
FIG. 4 is a cross section illustration of the medical balloon apparatus of FIG. 1 in an expanded, deployed state, including a balloon body of a first configuration.

FIG. 4 is a cross section illustration of the medical balloon apparatus 102 in an expanded, deployed state, including a balloon body 112 of a first configuration. The balloon body 112 is formed by a wall 402 which may be described as having a proximal wall 404, a distal wall 406, one or more central or side walls 416 between the proximal wall and the distal wall, and a wall thickness 408. The balloon body 112 has a maximum diameter 410 defined as the largest distance between the proximal wall 404 to distal wall 406, and an internal volume 412 defined as the space bounded by the wall 402. The maximum diameter 410 of the balloon body 112 when inflated is large by medical device standards and may be between 5 cm to 20 cm. In use, the maximum size of the balloon depends on the amount of assistance that might be needed as labor progresses. The interval volume of the balloon body 112 when inflated is also large by medical device standards and may be up to a maximum of 3 liters of volumetric displacement within the balloon body 112.

The walls 402, 404, 406 of the balloon body 112 are made of a soft, flexible, and durable biocompatible material that allows the balloon body to expand to a predetermined shape while withstanding high pressures upon inflation and force application. At the same time, the walls 402, 404, 406 of the balloon body 112 are thin and flexible enough to allow the balloon body to collapse upon deflation to a size and shape that is flexible enough to contort along a described delivery path.

During transition from the collapsed state shown in FIG. 1 and the expanded state shown in FIG. 4, the balloon body 112 expands in the direction of the longitudinal axis 414 of the conduit body 106 away from the distal tip 316 of the conduit body. The balloon body 112 also expands in an asymmetric fashion so as to curve back toward the conduit body 106.

The balloon body 112 may be configured to distribute forces 422 and direct the degree of expansion of the balloon body in a direction predominantly through a particular wall of the balloon body. Such balloon body 112 configuration may be provided through one of wall thickness design, material property design, or a combination of wall thickness and material property designs.

In one design, the balloon body 112 may be configured such that the thickness of the central walls 416 is less than the thickness of the proximal wall 404 and the distal wall 406. The thickness of the distal wall 406 may be greater than or equal to the thickness of the proximal wall 404. In this design, the central walls 416 are more elastic than the other walls and thus experience a greater degree of expansion upon inflation, relative to the other walls 404, 406. Accordingly, the balloon body 112 deforms to a greater extent in the proximal direction 424. This greater extent of expansion of the balloon body 112 in the proximal direction 424, in turn, results in a greater concentration and output of distributed force 422 in the proximal direction 424.

In another design, the walls 402, 404, 406 of the balloon body 112 may have a constant wall thickness 408 throughout and balloon expansion is controlled through the use of different materials having different stiffness/elasticity properties. To this end, the central walls 416 may be formed of a material having less stiffness (higher elasticity) than that of the proximal wall 404 and the distal wall 406. The elasticity of the distal wall 406 may be greater than or equal to the elasticity of the proximal wall 404. In one configuration, the proximal wall 404 and the distal wall 406 may be formed of mylar, and the central walls 416 formed of latex. In this design, the central walls 416 again experience a greater degree of expansion upon inflation such that the balloon body 112 deforms to a greater extent in the proximal direction 424. This greater extent of expansion of the balloon body 112 in the proximal direction 424, in turn, results in a greater concentration and output of distributed force 422 in the proximal direction.

In another design, the balloon body 112 may be made of differing materials with different mechanical properties or a differing thickness to control the direction of distribute forces 422 and direct the degree of balloon body expansion in a direction predominantly through a particular wall of the balloon body. For example, the proximal wall 406 may be constructed of thin mylar to reduce the amount of excursion and expansion of this portion of the balloon body 112, while the central walls 416 may be constructed of thin polyurethane, that allows for a greater degree of expansion by the central walls 416 relative to the other walls 404, 406 of the balloon body 112 to thereby limit the amount of forces applied through the central walls 416 and the amount of pressure being exerted against the uterine wall(s), placenta or other internal intrauterine structures that may be adjacent the central walls.

Figure 5A:
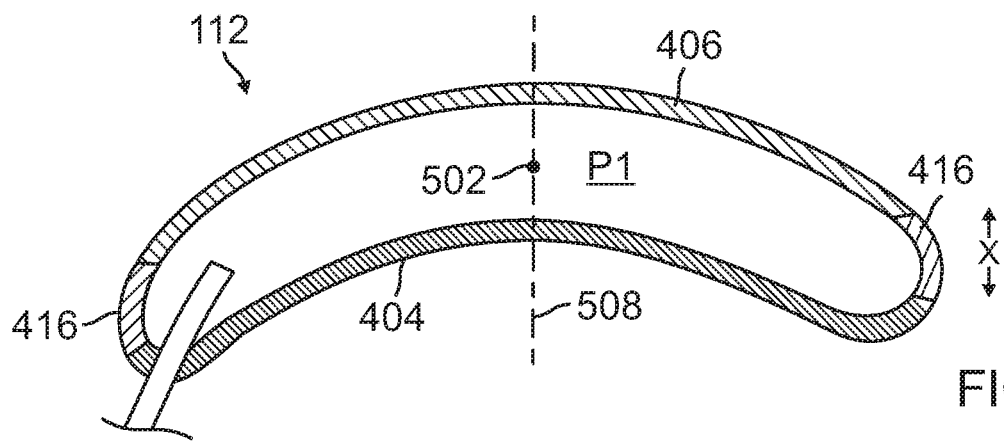
FIGS. 5A-5C are schematic illustrations of a balloon body at different stages of expansion.
Figure 5B:
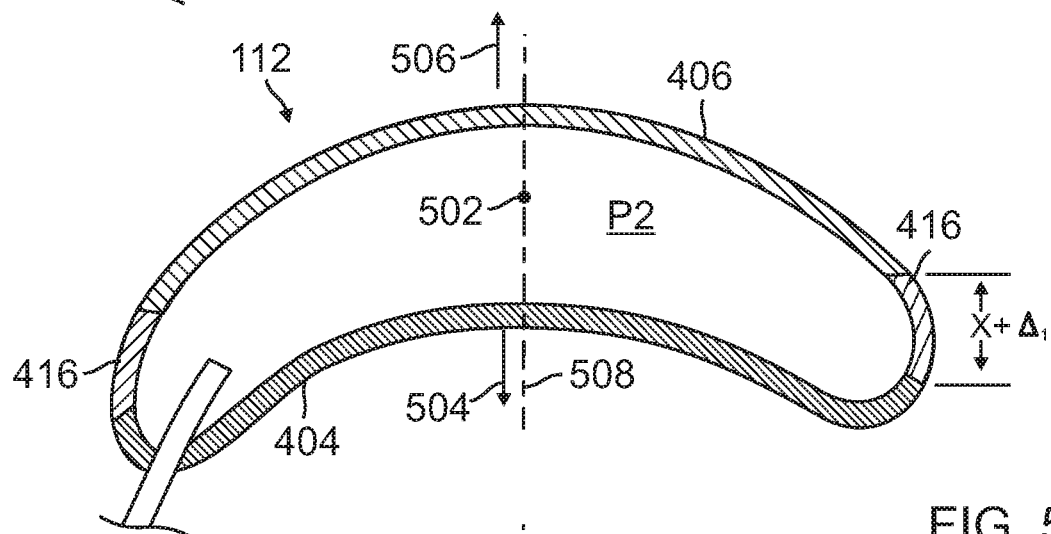
Figure 5C:
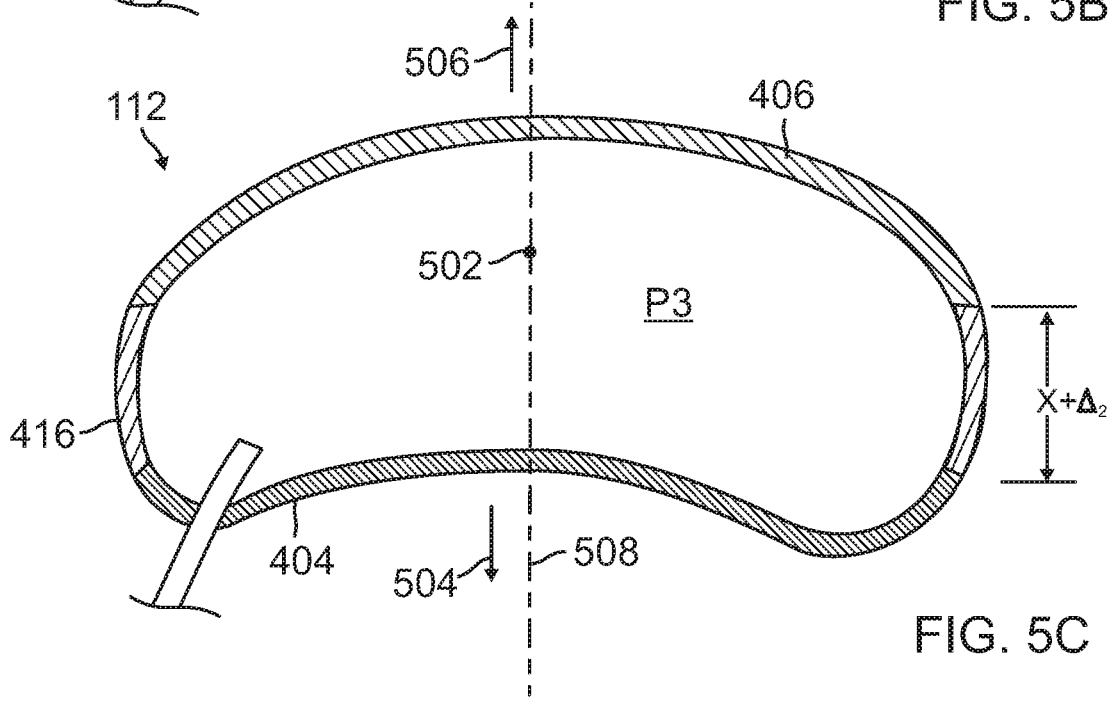

FIGS. 5A-5C are schematic illustrations of a balloon body 112 at different stages of expansion. The balloon body 112 includes central walls 416 configured to be more elastic than the proximal wall 404 and the distal wall 406. The balloon body 112 is characterized by an axis 508 of expansion which corresponds to the axis/direction along which the balloon predominantly expands during inflation. FIG. 5A corresponds to an expansion stage of the balloon body 112 at a first internal pressure P1, wherein the central walls 416 have a length dimension x.

FIG. 5B corresponds to an expansion stage of the balloon body 112 at a second internal pressure P2 that is greater than the first internal pressure P1. At the second internal pressure P2 the central walls 416 of the balloon body stretch to a dimension x+Δ1. The change in dimension of the central walls 416 results in expansion of the balloon body 112 and movement of both the proximal wall 404 and the distal wall 406 in generally opposite directions relative to each other and along the axis 508. For example, with respect to fixed point 502 on the axis 508, the distal wall 406 is displaced in a first direction 506 while the proximal wall 404 is displaced in a second direction 504. The amount by which the proximal wall 404 is displaced is greater than the amount by which the distal wall 406 is displaced. In other words, the degree of displacement of the proximal wall 404 exceeds the degree of displacement of the distal wall 406.

FIG. 5C corresponds to an expansion stage of the balloon at a third pressure P3 that is greater than the second pressure P2. At the third pressure P3 the central walls 416 of the balloon body 112 stretch to a dimension x+Δ2. The change in dimension of the central walls 416 results in further expansion of the balloon body 112, and corresponding displacement of the distal wall 406 in the first direction 506 and displacement of the proximal wall 404 in the second direction 504. Again, with respect to point 502 along the axis 508, the displacement of the proximal wall 404 exceeds the displacement of the distal wall 406.

Figure 6:
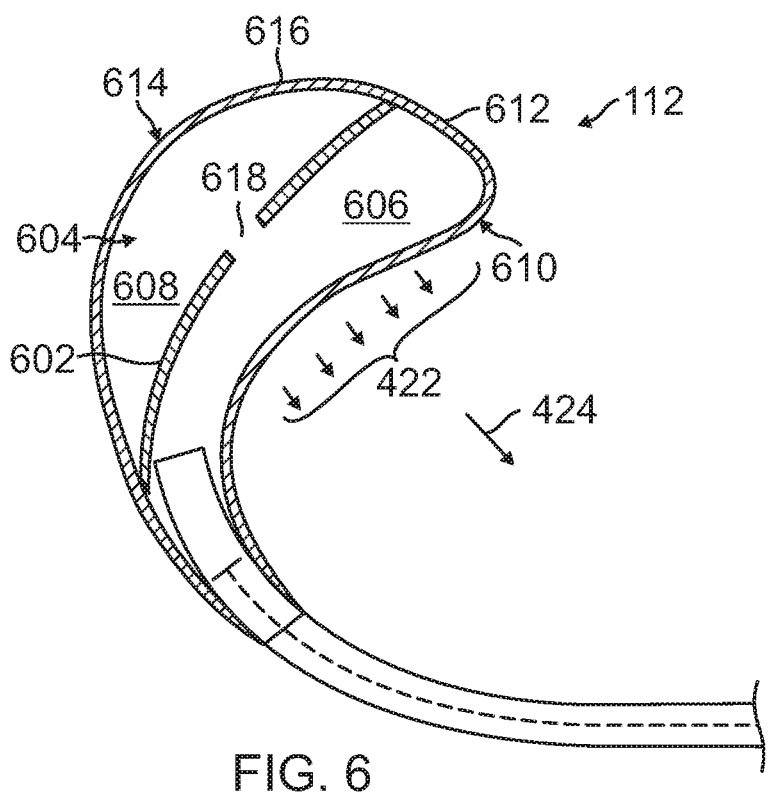
FIG. 6 is a cross section illustration of the medical balloon apparatus of FIG. 1 in an expanded, deployed state, including a balloon body of an alternate configuration.

FIG. 6 is a cross section illustration of the medical balloon apparatus 102 in an expanded, deployed state, including a balloon body 112 of an alternate configuration. In this design, the balloon body 112 contains one or more tension bearing structures 602 located within the interior chamber 604 of the balloon body 112. These one or more tension structures 602 span the interior chamber 604 to thereby create one or more interior sub-chambers. In the configuration shown in FIG. 6, the interior chamber 604 is divided into a first sub-chamber 606 and a second sub-chamber 608 by a single tension bearing structure 602. The tension structures 602 may include one or more openings 618 through which pressurized agent passes between adjacent sub-chambers 606, 608.

While the configuration shown in FIG. 6 has one tension bearing structure 602, more than one tension bearing structure may be included. In this design, the balloon body 112 may be described as having a first sub-balloon 610 having a first sub-balloon wall 612, and a second sub-balloon 614 having a second sub-balloon wall 616. The first sub-balloon wall 612 and the second sub-balloon wall 616 may be constructed, through one or more of a wall thickness characteristic and a material property characteristic, such that the first sub-balloon wall 612 experiences a greater degree of expansion than the second sub-balloon wall 616. As such, a greater extent of expansion of the balloon body 112 in occurs in the proximal direction 424, in turn, results in a greater concentration and output of distributed force 422 in the proximal direction 424

Figure 7:
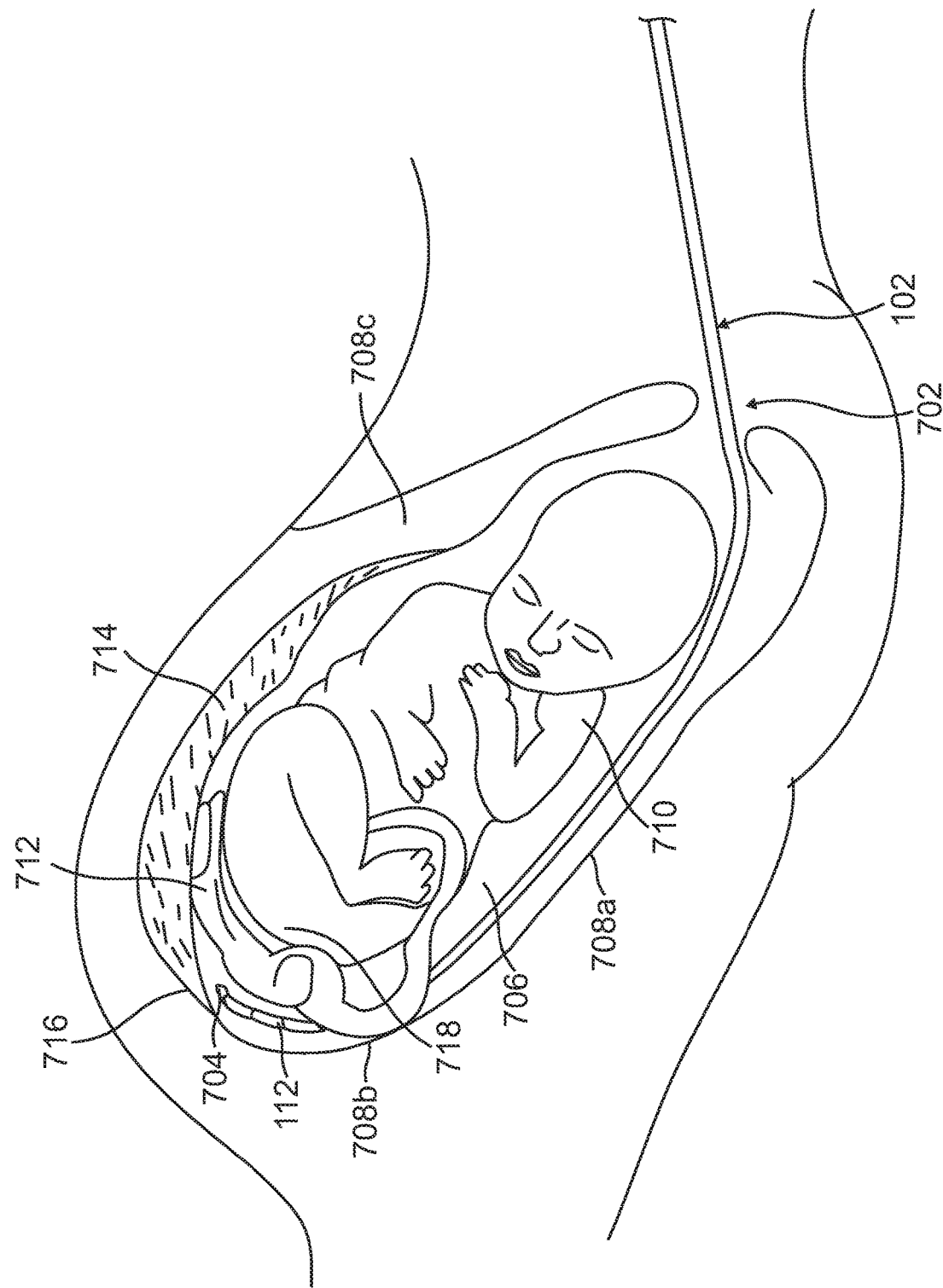
FIG. 7 is an illustration of the medical balloon apparatus of FIG. 1 positioned in an intrauterine cavity, in a collapsed, pre-deployed state.

FIG. 7 is an illustration of the medical balloon apparatus 102 positioned in an intrauterine cavity, while in a collapsed, pre-deployed state. During maternal labor upon desired use of the medical balloon apparatus 102, the packaged, pre-deployed balloon apparatus is inserted via the cervical canal 702 and the distal tip 704 of the balloon body 112 is navigated within the uterine cavity space 706 and along the uterine walls 708a, 708b, 708c to circumnavigate the fetus 710, umbilical cord 712, and placenta 714 until the balloon body 112 is placed at a target location near the fundus 716 of the uterus. As shown, this location is proximal to the fetus 710 and birth canal, within a uterine cavity space adjacent to the base 718 of the fetus with a cephalic presentation.

Insertion, navigation, and placement of the medical balloon apparatus 102 may be performed using an access catheter 200, such as shown in FIG. 2, and further described in co-pending U.S. patent application Ser. No. 14/942,577, titled "Intrauterine Access Catheter For Delivering and Facilitating Operation of a Medical Apparatus For Assisting Parturition". To aid in proper orientation of the medical balloon apparatus 102 so the proximal wall 404 is facing the infant, the access catheter 200 includes markers that provide an indication of both direction and depth of insertion of the catheter. The balloon body 112 may include similar markers on the proximal wall 404. Furthermore, the torque rigidity of the conduit body 106 is high enough so that the rotations along the conduit result in rotation of the pre-inflated balloon. Accordingly, the user may ensure proper orientation of the balloon body 112 based on the orientation of the markers on the access catheter 200, and possible additional markers on the balloon body 112.

Figure 8:
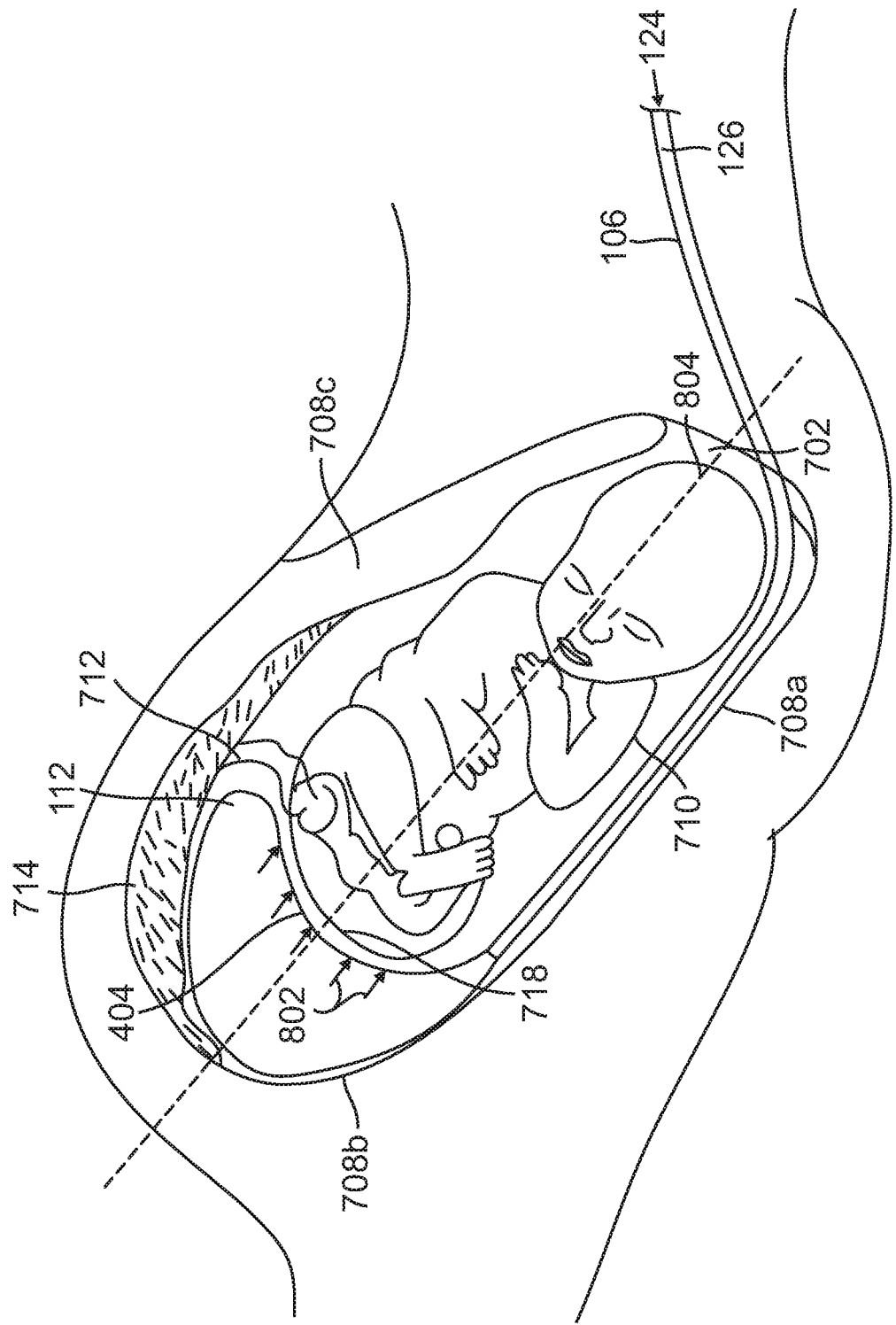
FIG. 8 is an illustration of the medical balloon apparatus of FIG. 1 positioned in an intrauterine cavity, in an expanded, deployed state.

FIG. 8 is an illustration of the medical balloon apparatus 102 positioned in an intrauterine cavity, while in an expanded, deployed state. After placement of the distal tip of the balloon body 112 at the targeted location, the balloon is deployed by injection of pressurized agent 124 through the internal lumen 126 of the conduit body 106. The balloon body 112 expands to reach pressure equilibrium. Injection of the pressurized agent 124 into the internal lumen 126 causes the balloon body 112 to expand predominantly in the direction of the cervical canal 702. This expansion of the balloon body 112 results in the application of distal forces 802 towards the base 718 of the fetus 710 and towards the cervical canal 702. FIG. 8 shows the balloon body 112 during expansion relative to the fetus 710, umbilical cord 712, placenta 714, uterine walls 708a, 708b, 708c, and cervical canal 702.

Throughout inflation of the balloon body 112, the proximal wall 404 of the balloon body faces the fetus 710 and cervical canal 702. Due to the previously described designs of the balloon body 112, the balloon body predominantly expands in the direction generally along an axis 804 passing through the uterus and the cervical canal 702. Accordingly, directional forces 802 resulting from expansion of the balloon body 112 are applied to the base 718 of the fetus. As the fetus 710 descends, the balloon body 112 is further expanded in order to maintain the application of the directional forces 802. As such, directional forces 802 are applied throughout infant descent through the cervical canal 702. Predominant expansion of the balloon body 112 in the direction along the axis 804 in the direction of the cervical canal 702 reduces expansion of the balloon body in other directions. This is beneficial in that it reduces the amount of forces applied to other intrauterine structures, e.g., the uterine walls 708a, 708b, 708c, and parts of the fetus 710 other than the base 718.

Figure 9:
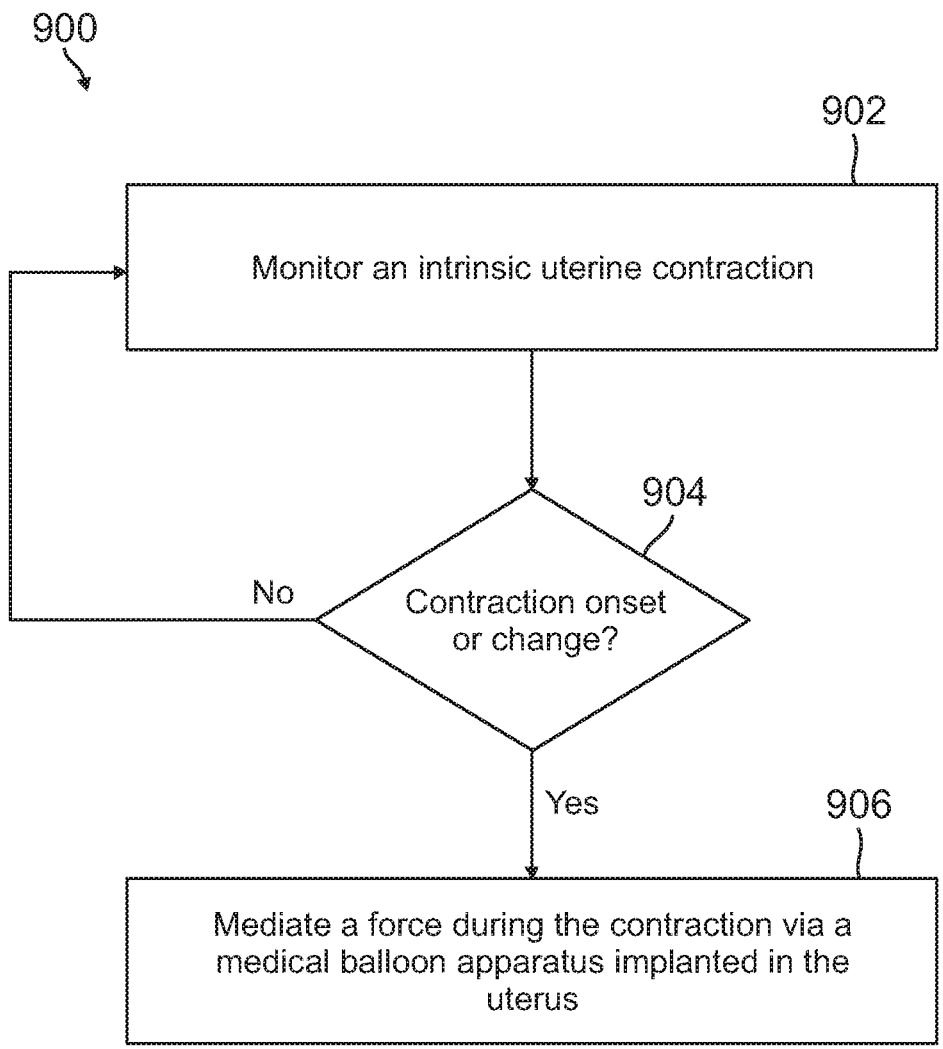
FIG. 9 is a flow chart of a method of augmenting expulsive uterine forces towards a cervical canal during delivery of a fetus from a uterus.

FIG. 9 is a flow chart of a method of augmenting expulsive intrinsic uterine forces towards a cervical canal during delivery of a fetus from a uterus. The method may be performed by the medical balloon system 100 of FIG. 1.

At step 902, the system 100 monitors an intrinsic uterine contraction. The intrinsic uterine contraction may be an onset of a contraction or it may be a change in state of an occurring contraction that results in either an increase in intrinsic intrauterine pressure or forces or a decrease in intrinsic intrauterine pressure or forces. The onset and pressure state of a uterine contraction may be monitored for by the controller 104 based on electrical activity sensed from the uterus and the processing of the sensed electrical activity. For example, morphology analysis of the sensed electrical activity may detect an onset of a contraction and changes in the pressure state of the contraction. The onset and pressure state of a uterine contraction also may be monitored for by the controller 104 based on sensed pressures. In one configuration, pressures are sensed through the conduit body 106, wherein such pressures are indicative of pressure within the uterus. In another configuration, an intrauterine pressure measurement may be obtained from a pressure sensor associated with a medical balloon apparatus 102 that is delivered in the uterus.

At step 904, if an onset of an intrinsic uterine contraction or a change in state of an ongoing contraction is not detected by the system 100, the process returns to step 902. If onset of an intrinsic uterine contraction or a change in state of an ongoing contraction is detected, the process proceeds to step 906, where the system 100 mediates a force generated via a medical balloon apparatus 102 located in the uterus. The force is directed toward the cervical canal and augments natural expulsive uterine forces. In one configuration, the medical balloon apparatus 102 includes a balloon body 112 positioned at a proximal uterine location adjacent the fetus. For example, as shown in FIG. 8, the balloon body 112 may be positioned between the base 718 of the fetus 710 and the fundus 716. The force is generated by delivering an agent to the balloon body 112 to thereby expand the balloon body toward the cervical canal 702 and into contact with the base 718 of the fetus 710.

Upon either of a detection of an onset of an intrinsic uterine contraction, or an increase in uterine contraction forces, the system 100 may mediate the force by delivering an agent to the balloon body 112 to at least partially expand the balloon body toward the cervical canal 702 and into contact with the base 718 of the fetus 710. Upon a detection of a decrease in uterine contraction forces, the system 100 may mediate the force by discharging an agent from the balloon body 112 to at least partially collapse the balloon body away from the fetus 710 and the cervical canal 702. As a safety measure, the system 100 may also mediate the force by discharging an agent from the balloon body 112 when a measured pressure associated with the medical balloon apparatus exceeds a threshold value, such as 200 mmHg.

The forces applied by the medical balloon apparatus 102 are mediated by increasing and decreasing the agent delivered through the conduit body for constructively augmenting uterine pressures generated by intrinsic contractions. The target pressure or pressure based objective is set within the controller 104 and used for defining the target balloon pressure resulting from agent delivery. To this end, the controller 104 may include a memory for storing program code and a processor that operates in accordance with the code to implement the process of FIG. 9. Accordingly, the controller 104 may be considered a special purpose computer that is configured to—in conjunction with a medical balloon apparatus 102 having a balloon body 112 configured to be positioned in the uterus—monitor an intrinsic uterine contraction, and mediate a force generated via the balloon body during the intrinsic uterine contraction, wherein the force is directed toward the cervical canal and augments natural expulsive uterine forces.

The controller 104 is further configured to implement subprocesses associated with monitoring and mediating. For example, the controller 104 may be configured to monitor an intrinsic uterine contraction by obtaining one or more of pressure signals and electrical signals indicative of an intrinsic uterine contraction. As described above, these signals may be provided by sensors associated with the medical balloon apparatus. The controller 104 includes program code that allows the processor of the controller to detect at least one of an onset of an intrinsic uterine contraction, an increase in uterine contraction forces, and a decrease in uterine contraction forces based on the one or more of pressure signals and electrical signals. To this end, the controller may process the signals to obtain corresponding measurements and compare the measurements to threshold values stored in memory that represent a contraction onset, or a change (e.g., increase or decrease) in uterine contraction force that warrants mediation.

With respect to mediation, the controller 104 may be configured to deliver an agent to the balloon body 112 to at least partially expand the balloon body toward the cervical canal and into contact with the fetus upon either of a detection of an onset of an intrinsic uterine contraction, or an increase in uterine contraction forces. The controller 104 may be configured to discharge an agent from the balloon body 112 to at least partially collapse the balloon body away from the fetus and the cervical canal upon a detection of a decrease in uterine contraction forces. As describe previously, an increase or decrease in uterine contraction forces may be warranted when the controller 104 detects a corresponding increase or decrease in pressure due to intrinsic uterine activity that satisfies a threshold criterion. The controller 104 may also be configured to discharge an agent from the balloon body 112 when a measured pressure associated with the medical balloon apparatus exceeds a maximum allowed threshold value.

The previous description is provided to enable any person skilled in the art to practice the various aspects described herein. Various modifications to these aspects will be readily apparent to those skilled in the art, and the generic principles defined herein may be applied to other aspects. For instance, the conduit body 106 and the internal lumen 126 geometry may vary depending on the catheter delivery system, the expanding balloon may vary within a range of sizes and shapes, and the balloon may have varying thicknesses or radius of curvatures, and the bidirectional conduit may utilize more than one lumen.

Furthermore, while the configuration described herein were with respect to a balloon apparatus in the form an inflatable membrane, other balloon apparatuses or expandable members may be employed. For example in an alternative configuration, the balloon apparatus/expandable member deployed from the distal tip of the catheter may be a gel based bio-compatible substance expulsed from the lumen of the catheter. The substance may configured to have a strong surface tension that enables pressure applications towards the infant and birth canal while conforming to the size and shape of the uterine space and infant. In yet another alternative configuration, the balloon apparatus/expandable member may be a viscous bio-compatible polymeric fluid with a memory shape causing the formation of a shape upon contact with one or more substances contained within the amniotic fluid.

Disclosed herein is an intracorporeal medical device 102 capable of monitoring and delivering pressure to the uterine wall or infant(s) for the purpose of managing the birthing delivery process. The medical device 102 is delivered to a target location in an intrauterine or extrauterine location adjacent to the uterine wall. The medical device 102 may be delivered to a target location with the use of a catheter, separate delivery system, or surgical insertion, and is deployed or inflated once it is at or near its targeted location. The medical device 102 administers therapies, pressure and/or forces, fluids, or therapeutic agents to assist the birthing process.

The medical device 102 together with a controller 104 form a medical system 100 that monitors the onset or occurrence of uterine contractions and other muscle activity including abdominal contraction. The medical system 100 times the delivery of therapy including the direction and degrees of applied forces relative to the occurrence of natural uterine contractions or other muscle activity during labor. The medical system 100 may incorporate physiologic mechanical measures of birthing resistance including fetal-pelvic, fetal-birth canal, or fetal-uterine pressures. The medical system 100 may employ one or more mechanisms to vary the direction and magnitude of forces applied to the uterine walls, fetus, or other anatomical structures. The medical system 100 may include markers on the medical device 102 that enable visualization of the intrauterine cavity during the birthing process including geometrical relationships of the uterine wall, birth canal, one or more infant(s), placenta, or umbilical cord(s).

The medical device 102 includes a balloon body 112 that is made from silicone, polyvinyl chloride, latex, or other similar substance capable of being inflated and deflated, or applying pressure in a reliable repeatable manner while maintaining pliability. The medical device 102 may include one or more sensors for detecting and monitoring intrauterine forces and directions due to passive uterine and abdominal stretch, abdominal muscle contractions, myometrial uterine muscle contractions, or other externally actively applied forces. These sensors may be located on the balloon body 112 or the conduit body 106 of the medical device 102. The medical system 100 utilizes algorithms for defining upper levels of applied pressure levels to reduce the likelihood of damage to the infant or maternal organs specifically the infant head and shoulders, and maternal uterine cavity, birthing canal, umbilical cord, and placenta. The medical system 100 also utilizes sensors and algorithms for monitoring indices of physiologic birthing including infant heart rates, maternal stress measures, umbilical cord flow, infant perfusion. The medical device 102 and system 100 may be used acutely to assist the intrapartum delivery process, or chronically to monitor and manage the prepartum to intrapartum periods of the birthing delivery process.

Thus, the claims are not intended to be limited to the aspects shown herein, but is to be accorded the full scope consistent with the language claims, wherein reference to an element in the singular is not intended to mean "one and only one" unless specifically so stated, but rather "one or more." The word "exemplary" is used herein to mean "serving as an example, instance, or illustration." Any aspect described herein as "exemplary" is not necessarily to be construed as preferred or advantageous over other aspects. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

What is claimed is:

1. A system for augmenting expulsive uterine forces towards a cervical canal during delivery of a fetus from a uterus, the system comprising:
   a medical balloon apparatus having a balloon body configured to be positioned in the uterus, the balloon body configured to transition between a compacted state and an expanded state;
   a sensor configured to obtain signals indicative of intrinsic uterine contractions; and
   a controller coupled to the medical balloon apparatus and the sensor and configured to:
      monitor an intrinsic uterine contraction based on the obtained signals; and
      mediate a force generated via the balloon body during the intrinsic uterine contraction, wherein the force is directed toward the cervical canal and augments natural expulsive uterine forces.

2. The system of claim 1, wherein the medical balloon apparatus comprises an internal lumen and the sensor comprises a pressure sensor configured to sense pressure within either of the internal lumen or the balloon body.

3. The system of claim 1, wherein the sensor comprises an electrical sensor.

4. The system of claim 3, wherein the electrical sensor is part of the medical balloon apparatus.

5. The system of claim 3, wherein the electrical sensor comprises an external electrical sensor that is independent of the medical balloon apparatus.

6. The system of claim 3, further comprising an access catheter configured to receive the medical balloon apparatus, wherein the electrical sensor is part of the access catheter.

7. The system of claim 1, wherein the controller monitors an intrinsic uterine contraction by being further configured to:
   detect at least one of an onset of an intrinsic uterine contraction, an increase in uterine contraction forces, and a decrease in uterine contraction forces based on the obtained signals.

8. The system of claim 7, wherein the controller mediates a force by being further configured to:
   deliver an agent to the balloon body to at least partially expand the balloon body toward the cervical canal and into contact with the fetus upon either of a detection of an onset of an intrinsic uterine contraction, or an increase in uterine contraction forces.

9. The system of claim 7, wherein the controller mediates a force by being further configured to:
   discharge an agent from the balloon body to at least partially collapse the balloon body away from the fetus and the cervical canal upon a detection of a decrease in uterine contraction forces.

10. The system of claim 7, wherein the controller mediates a force by being further configured to discharge an agent from the balloon body when a measured pressure associated with the medical balloon apparatus exceeds a threshold value.

* * * * *